United States Patent [19]

Warzywoda et al.

[11] Patent Number: 4,762,788
[45] Date of Patent: Aug. 9, 1988

[54] PROCESS FOR PRODUCING CELLULOLYTIC ENZYMES

[75] Inventors: Michel Warzywoda, Rueil Malmaison; Véronique Ferré, Boulogne Billancourt; Jacques Pourquie, Palaiseau, all of France

[73] Assignee: Institut Francais du Petrole, Rueil-Malmaison, France

[21] Appl. No.: 675,595

[22] Filed: Nov. 28, 1984

[30] Foreign Application Priority Data

Nov. 29, 1983 [FR] France ................. 83 19184

[51] Int. Cl.$^4$ .................. C12N 9/42; C12N 1/14
[52] U.S. Cl. ...................... 435/209; 435/254; 435/945
[58] Field of Search .......... 435/209, 254, 945

[56] References Cited

U.S. PATENT DOCUMENTS 3,972,775  8/1976  Wilke et al. ............ 435/209
4,275,163  6/1981  Gallo ...................... 435/209
4,472,504  9/1984  Gallo ...................... 435/209

OTHER PUBLICATIONS

Mandels, *Annual Reports on Fermentation Processes*, vol. 5, (1982), pp. 35–78.
Allen et al., *Biotechnology and Bioengineering Symp.*, No. 12, 451–459, (1982).
Warzywoda et al., *Biotechnology Letters*, vol. 5, No. 4, (1983), pp. 243–246.
Montenecourt et al., *Applied Environmental Microbiology*, vol. 34, (1977), pp. 777–782.
Allen et al., *Biotechnology and Bioengineering*, vol. 23, (1981), pp. 2641–2645.
Frein et al., *82nd Annual Meeting of the American Society for Microbiology*, Atlanta, Ga., Mar. 7–12, (1982).

*Primary Examiner*—Charles F. Warren
*Assistant Examiner*—Elizabeth A. Hanley
*Attorney, Agent, or Firm*—Millen & White

[57] ABSTRACT

This invention concerns a process of producing cellulolytic enzymes by fermentation with the *Trichoderma reesei* fungus.

This process includes two steps:
(a) a first step of subjecting to aerobian fermentation a culture medium comprising a strain of *Trichoderma reesei*, nutrition compounds and a small quantity of cellulose and sugar,
(b) a second step of contining the aerobian fermentation by adding soluble sugar at a speed such that the sugar concentration in the fermentation zone remains under 0.3% by weight.

The cellulolytic enzymes obtained are used in the enzymatic hydrolysis of a lignocellulosic biomass.

10 Claims, No Drawings

PROCESS FOR PRODUCING CELLULOLYTIC ENZYMES

This invention concerns a process for producing enzymes capable of hydrolyzing cellulose and hemicelluloses. It concerns more particularly a process, preferably operating continuously, for manufacturing cellulolytic enzymes, hereinafter called "cellulase" or "cellulases", by fermentation of the *Trichoderma reesei* fungus.

BACKGROUND OF THE INVENTION

The lignocellulosic biomass forms a large reserve, as yet underused, of fermentable sugars. These sugars may be obtained by hydrolysis of cellulose and of hemicelluloses present in a large amount in said biomass.

Processes for hydrolysing cellulose and hemicelluloses have already been proposed. An older one is chemical hydrolysis, generally performed by means of strong acids. The industrial development of such a process is difficult. More recently, numerous studies have been conducted which have led to enzymatic hydrolysis processes offering the advantage of avoiding degradation of potential sugars present in the biomass. Such a technology, in order to be used on industrial scale, requires large amounts of cellulases. A systematic experimentation has led to the discovery of a continuous process for manufacturing cellulases under efficient and cheap conditions, whereby the enzymatic hydrolysis of the lignocellulosic biomass may be considered as industrially feasible.

Amongst various microorganism known to excrete cellulases, the *Trichoderma reesei* ascomycete fungus is considered as one of the more adapted to an industrial production of theses enzymes: Mandels, Annual Reports on fermentation processes vol. 5, G. Tsao Editor, Academic Press N.Y. 1981, p. 35-78.

The wild strains of this fungus have the capacity to excrete, in the presence of cellulose, the mixture of all the enzymatic activities subsequently required for hydrolysing the lignocellulosic biomass. The resultant cellulases have exo- and endo-glucanase, $\beta$-glucosidease, exo- and endo-xylanase and $\beta$-xylosidase activity. The main prior works concern improvements to wild strains by conventional genetic techniques of mutation-selection, which led to the formation of hyperproducing strains of *Trichoderma reesei*, such as MCG 77 (deposited at the Northern Regional Research Center, Ill., under serial number NRRL 11, 236) disclosed by Gallo in U.S. Pat. No. 4,275,163; MCG 80 disclosed by Allen, A. L. and Andreotti, R. E., Biotechnology and bioengineering Symposium No.12, pages 451-459 (1982); RUT C 30 disclosed by Montenecourt, B. S. and Eveleigh, D. E., Applied Environmental Microbiology, volume 34, page 777 (1977) and CL 847 disclosed By Warzywoda, M., at al, Biotechnology Letter, volume 5, page 243 (April 1983).

This genetic improvement has provided strains having a maximum productivity of excreted cellulases as well as a decreased catabolic repression as compared to that of the wild strain. This catabolic repression is a determinant factor in the production of cellulases on industrial scale; as a matter of fact, the synthesis of cellulases is blocked by the presence, in the culture medium, of easily metabolizable sugars. The various above-mentioned strains have been the object of research and development work which have confirmed their superiority as compared to the wild strain for cellulase excretion. Mandels, above cited, has shown that, as for the wild strain, higher enzyme productions are obtained by feeding these strains with purified celluloses as the main source of energy and carbon. Under these conditions, the cellulase production is proportional to the amount of cellulose added to the medium, at least as far as this cellulose does not result in too high a viscosity of the medium, which no longer allows normal efficiency in the different transfers required for the cultivation. It is thus accepted that the maximum achievable concentration of cellulose is about 70-80 g/l for example. These culture media of high purified cellulose content cannot be extrapolated to industrial scale in view, on the one hand, of the high cost of purified cellulose and, on the other hand, of the high power consumption for stirring culture media of very high viscosity.

Searches for carbon sources providing easier extrapolation for the culture media have thus been made. Allen, A. L. and Mortensen, R. E., Biotechnology and Bioengineering, volume 23, pages 2641-2645 (1981) have proposed as carbon sources several sugars used alone or as mixtures, in an view of their low cost and their high solubility in aqueous medium. However, it is observed that the cellulase production obtained by cultivating *Trichoderma reesei* on culture media based on soluble sugars is much lower than that obtained on cellulose, particularly on purified cellulose. This low production is probably attributable to a repressing effect of sugars, at the prevailing concentrations, on the production of enzymes.

Techniques for the continuous feeding of a carbonaceous substrate have been used to feed microorganisms with the sugar amounts strictly required for their needs, and to limit the residual sugar content in the cultures, thus preventing the catabolic repression due to sugars. The use of these techniques with non soluble cellulosic substrates raises the problem of extrapolation under sterile conditions. Thus attempts have been made to use these techniques with soluble sugars whose concentrated solutions may be easily sterilized and introduced under sterile conditions by pumping or by any other liquid transfer means into reactors of variable capacity. Allen and Andreotti, above mentioned, have used a source of lactose, soluble sugar, as carbon source for the strain MCG 80 *Trichoderma reesei*, whereas Allen and Mortensen, above-mentioned, have used glucose, cellobiose or mixtures of artificial sugars with the strain RUT C 30 *Trichoderma reesei*. The results obtained by these authors, concerning the content, the yield as well as the productivity of cellulase in continuous operation, although higher than those obtained in batch on the same substrates, do not reach however those obtained in batch on purified celluloses.

SUMMARY OF THE INVENTION

The present patent application provides for cellulases production with high yields and enzymes contents.

Unexpectedly, it has been found possible, by means of a particular start-up of the feeding (preferably continuous) with substrate (Fed-Batch), using soluble sugars such as lactose, glucose, xylose, arabinose, cellobiose or their mixtures as a carbon source, to obtain a production of cellulases with enzyme contents clearly higher than those obtained by the prior art technologies, particularly those operating in batch mode on purified cellulose, as well as a significant improvement of the enzyme production in proportion to the mass of substrate involved.

Thus, the invention concerns a process for aerobic production of cellulase by cultivating a *Trichoderma reesei* strain in a fermentation zone containing a nutrient medium. This process consists of feeding said fermentation zone, preferably in a continuous manner, with an aqueous solution of at least one soluble sugar, preferably lactose. Said process is characterized by:

(a) A first step of subjecting an aerobic fermentation a culture medium comprising a strain of *Trichoderma reesei*, inorganic salts and, as an initial carbonaceous substrate, at least one cellulose containing material, for example paper pulp or purified cellulose, and at least one soluble sugar, preferably lactose, the amount by weight of said cellulose and said soluble sugar, in proportion to the culture medium, being each 0.01-2% (i.e. about 0.1-20 grams per liter of solution) and the first step being continued without further addition of soluble sugar for a time sufficient to consume at least 10% of the sugar, preferably at least 20% and to obtain a sugar concentration of the medium lower than 0.3% by weight, preferably lower than 0.2%, and (b) A second step of continuing the aerobic fermentation by adding soluble sugar in a progressive manner, so as to introduce a sugar amount totalling at least 3% by weight of the culture medium while maintaining the sugar concentration of said culture medium at less than 0.3% by weight, preferably 0.1-0.25% by weight.

The cellulose concentration is preferably 0.2-2% by weight, more preferably 0.5-1% by weight and the sugar concentration 0.02-1% by weight. The sugar concentration is preferably 10-50% of the cellulose concentration.

The process of the invention consists of achieving most of the growth and of the production of enzymes by *Trichoderma reesei* with a feed of soluble sugar, for example lactose, preferably continuous, the maximum enzyme production being obtained by the previous incorporation into the culture medium, before seeding thereof, of a small but critical amount of cellulosic inductor. For this purpose, the preculture contained in the fermenter is maintained in contact with a cellulosic inductor before adding the sugar solution into the fermenter.

Conventionally, a liquid preculture is prepared from spores or mycelium of the selected *Trichoderma reesei* strain, in a culture medium containing the usual mineral salts and vitamin complements and a carbon and energy source preferably as soluble sugars, preferably lactose. This preculture may be performed, for example, in a stirred flask placed in an enclosure at a constant temperature of about 27° C. or, preferably, in a fermenter. When the development of this preculture gives a biomass corresponding for example to 0.5-1.5% by weight of dry material of the culture medium, preferably 1%, the preculture is transferred, under sterile conditions, into the fermenter for enzyme production. This fermenter for enzyme production, according to the invention, contains a culture or nutrient medium comprising mineral salts, usual vitamin complements and surfactants, an amount of cellulosic inductor (e.g. purified cellulose, paper pulp) of 0.01-2%, preferably 0.5-1% by weight with respect to the culture medium, and a small amount of at least one sugar, as above explained. The necessary contact between the preculture and the medium containing the cellulosic inductor is maintained and then the reactor is fed, preferably continuously, with a sterile aqueous solution of at least one sugar, having a sugar concentration of about 20-30% by weight, this solution generally containing also a culture or nutrient medium, the feeding rate being adjusted as above-mentioned. This feeding with soluble sugar corresponds to soluble sugar concentration (expressed as total sugar weight added per final reaction volume) of, for example and preferably, 80-120 g/l over a period of about 90-160 h and, by way of illustration, more particularly about 100 g/l for a period of about 140 hours.

EXAMPLES

The invention will be better understood from the following non-limitative examples:

EXAMPLE 1 (comparative)

A prepared aqueous solution of inorganic salts, called C1, has the following composition: 3.32 g/l of potassium hydroxide (KOH), 4 ml/l of 85% phosphoric acid, 5.6 g/l of ammonium sulfate $(NH_4)_2SO_4$, 1.2 g/l of magnesium sulfate $MgSO_4$, $7H_2O$), 1.2 g/l of calcium chloride $(CaCl_2)$, 6.4 mg/l of manganese sulfate $(MnSO_4)$, 5.6 mg/l of zinc sulfate $(ZnSO_4, 7\ H_2O)$, 8 mg/l of cobalt chloride $(CoCl_2)$, 20 mg/l of iron sulfate $(FeSO_4, 7\ H_2O)$.

A fermenter containing 0.5 liter of solution C1, 1.4 liter of water, 2 g of yeast extract, 160 g of Whatman CC41 cellulose, 2 ml of Tween 80 (trade product), 2 ml of anti-foam, is sterilized by autoclaving for 20 minutes at 120° C. After cooling, the temperature of the medium is adjusted to 27° C. and the pH to a value of 5. The fermenter is then seeded with 200 ml of a liquid preculture of *Trichoderma reesei* CL 847 strain. The temperature is regulated to 27° C. for the 24 first hours and then to 25° C. until the need of the cultivation period. During the whole cultivation period, the pH is regulated to a value of 5 by addition of ammonia solution. The concentration of dissolved oxygen in the culture is maintained above 15% by weight of the saturating concentration by adjustment of the stirring speed and of the aeration rate. No nutrient except ammonia is added during the cultivation period. After 140 h of cultivation, the fermentation broth is collected and the analytic determinations are effected on aliquot parts of the supernatant fraction. The proteins content is titrated and the cellulases activity and β-glucosidase activity are determined respectively on filter paper and on cellobiose. 17.9 g/l of proteins, 13.7 international units of cellulases per milliliter (UPF/ml), 9.9 international units of β-glucosidase per millimeter have thus been obtained. 171 cellulases units per gram of carbon substrate were obtained.

EXAMPLE 2 (comparative)

Cultivation of *Trichoderma reesei* RUT 30 strain is conducted under conditions identical to those of example 1.

After 142 h, the following results are obtained: 14 g/l of proteins, 10 UPF/ml of cellulases activity, 5 U/ml of β-glucosidase activity. 125 units of cellulases per gram of carbon substrate have been obtained.

EXAMPLE 3 (comparative)

In this example, Whatman CC41 cellulose of examples 1 and 2 is replaced by a mixture of lactose with 10 g of paper pulp (cellulose). The fermenter is seeded with 200 ml of a preculture of *Trichoderma reesei* CL 847 strain. The cultivation is conducted under the same conditions as in exmaple 1. After 162 hours, the following results are obtained: 14.1 g/l of proteins, 8.4 UPF/ml of cellulases activity, 7.1 U/ml of β-glucosidase activity. 129 cellulases units have been obtained per gram of carbon substrate.

EXAMPLE 4 (comparative)

A culture of *Trichoderma reesei* RUT C 30 strain is conducted under conditions identical to those of example 3, After 162 h, the results are as follows: 10.2 g/l of proteins, 6.1 UPF/ml of cellulase activity, 3.3 U/ml of β-glucosidase activity. 94 cellulases units per gram of carbon substrate have been obtained.

EXAMPLE 5

A sterile aqueous solution is prepared which contains, for one liter, 250 g of lactose and 0.625 l of solution C1. It is called solution C2. A fermenter containing 0.5 l of solution C1, 1.3 l of water; 2 g/l of yeast extract, 2 ml of anti-foam, 2 ml of Tween 80, 25 g of paper pulp and 7.5 g of lactose (about 4.16 g/l) is sterilized in an autoclave for 20 minutes at 120° C.

After cooling, the temperature of the medium is adjusted at 27° C., the pH of the medium to a value of 5. The fermenter is then seeded with 0.2 l of liquid preculture of the *Trichoderma reesei* CL 847 strain. The temperature is regulated to 27° C. for the 24 first hours of cultivation, then at 25° C. until the end of the cultivation period. The pH is regulated to a value of 5 during the whole cultivation period by adding an ammonia solution. The concentration of oxygen dissolved in the culture is maintained above 15% by weight of the saturating concentration by adjusting the stirring speed and the aeration rate.

Lactose determinations are effected on culture samples at time intervals. After 23 hours, the lactose concentration in the fermentation broth is 1.2 g/l. The culture is then continuously fed under sterile conditions with solution C2; the feeding rate is so adjusted that the lactose concentration does not exceed 2 g/l during the whole cultivation period. The average lactose feeding rate is 1.9 g per hour up to the hundredth hour and 2.25 g per hour up to the end of the cultivation period. After 145 hours, one liter of solution C2 has been introduced in the culture. The feeding is then discontinued and the fermentation broth is collected. Analytic determinations on this broth give the following results: 36 g/l of proteins, 26.3 UPF/ml of cellulases activity, 34 U/ml of β-glucosidase. 246 cellulases units have been obtained per gram of carbon substrate.

EXAMPLE 6 (comparative)

The *Trichoderma reesei* CL 847 strain is cultivated under conditions identical to those of example 5, except for the feeding with solution C2 which is so conducted as to introduce one liter of said solution during the first 110 hours of cultivation. The residual lactose contents of the culture reach the respective values of 22 g/l at 40 hours and 6.5 g/l at 85 hours. After the end of the feeding with solution C2, at the 110$^{th}$ hour, the cultivation is continued up to the 160$^{th}$ hour. The results are the following: at the 110$^{th}$ hour: 13.6 g/l of proteins, 7.2 UPF/ml of cellulases activity, 7.3 U/ml of β-glucosidase; at the 145$^{th}$ hour: 14.4 g/l of proteins, 7.9 UPF/ml of cellulases activity, 7 U/ml of β-glucosidase. The experiment is continued up to 160 hours. No evolution occurs after the 145$^{th}$ hour. 67 cellulases units have been obtained per gram of carbon substrate.

EXAMPLE 7

The *Trichoderma reesei* RUT C 30 strain is cultivated under conditions indentical to those of example 5, solution C2 being continuously fed up to a total of one liter at the 145$^{th}$ hour. The lactose concentration never exceeds 2 g/l. The results are as follows: 29.5 g/l of proteins, 18.5 UPF/ml of cellulases activity, 13.2 U/ml of β-glucosidase. 173 cellulases units have been obtained per gram of carbon substrate.

EXAMPLE 8 (comparative)

The *Trichoderma reesei* RUT C 30 strain is cultivated under conditions identical to those of example 5, except for the addition of paper pulp which is omitted in the preparation of the medium before sterilization. Solution C2 is continuously fed up to a total of one liter at the 145$^{th}$ hour. The lactose concentration never exceeds 2 g/l. The results are the following: 18.4 g/l of proteins, 12.8 UPF/ml of cellulase activity, 8.7 U/ml of β-glucosidase. 132 cellulases units have been obtained per gram of carbon substrate.

EXAMPLE 9 (comparative)

A liquid preculture of *Trichoderma reesei* RUT C 30 strain is effected on 2% by weight of Whatman CC41 cellulose, as the only carbon and energy source. After 40 h, 200 ml of this preculture are transferred to a fermenter prepared as in example 1, except for Whatman CC41 cellulose, introduced only in an amount of 40 g into the medium before sterilization. The cultivation conditions are the same as in example 1. From the 42$^{th}$ hour to the 90$^{th}$ hour included, 8 g of sterile Whatman CC41 cellulose are added every eight hours; from the 98$^{th}$ to the 138$^{th}$ hour, 18.5 g of the same cellulose are added every eight hours. As a result of the repeated openings of the fermenter, required for the cellulose additions, a bacterial contamination appears as soon as the 70$^{th}$ hour. Since this contamination becomes more and more substantial, the operation cannot be continued beyond 138 hours. The results of the analytic determinations on the supernatant fractions of the culture collected after 138 hours are as follows: 24.3 g/l of proteins, 15.8 UPF/ml of cellulase activity, 10.2 U/ml of β-glucosidase activity. 159 cellulases units have been obtained per gram of carbon substrate.

EXAMPLE 10 (comparative)

*Trichoderma reesei* MCG 77 strain is cultivated under conditions identical to those of example 1, except that Whatman CC41 cellulose of example 1 is replaced by a mixture of lactose with 10 g of paper pulp (cellulose). The fermenter is seeded with 200 ml of a preculture of *Trichoderma reesei* MCG 77 strain. After 162 hours, the results are as follows: 4.8 g/l of proteins, 2.6 UPF/ml of cellulases activity, 1.2 U/ml of β-glucosidase activity, 40 cellulases units were obtained per gram of carbon substrate.

EXAMPLE 11

The *Trichoderma reesei* MCG 77 strain is cultivated under conditions identical to those of example 5. Solution C2 is continuously fed so as to introduce as a total one liter thereof up to the 148$^{th}$ hour. The lactose concentration never exceeds 2 g/l. The results are as follows: 22.6 g/l of proteins, 14 UPF/ml of cellulases activity, 5 U/ml of β-glucosidase activity. 131 units of cellulases were obtained per gram of carbon substrate.

What is claimed as this invention is:

1. A process for aerobic production of cellulase by cultivation of a *Trichoderma reesei* strain in a fermentation zone containing a nutrient medium, said process comprising feeding said fermentation zone with soluble sugar and being characterized by:
   (a) a first step of subjecting to aerobic fermentation conditions a culture medium comprising a Trichoderma reesei strain, an inorganic salt and an initial carbon substrate containing at least one cellulose containing material and at least one soluble sugar, the amount by weight of said cellulose and said soluble sugar, in proportion to the culture medium, being each 0.01–2%, the first step being continued without further soluble sugar addition for a sufficient time to consume at least 10% of the sugar and to obtain a sugar concentration in the medium lower than 0.3% by weight, and
   (b) a second step of continuing the aerobic fermentation by adding soluble sugar continuously so as to introduce a sugar amount totalling at least 3% by weight of the culture medium while maintaining the sugar concentration in said culture medium at a value lower than 0.3% by weight.

2. A process according to claim 1, wherein no cellulose-containing material is added during the second step.

3. A process according to claim 1, wherein the soluble sugar is lactose, glucose, xylose, arabinose, cellobiose or a mixture thereof.

4. A process according to claim 1, wherein the fermentation zone is fed with soluble sugar during the second step in a continuous manner.

5. A process according to claim 1, wherein the cellulose-containing material is paper pulp.

6. A process according to claim 1, wherein in step (a) the cellulose and sugar amounts are respectively 0.2–2% and 0.02–1% by weight and the contact is maintained until the sugar concentration becomes lower than 0.2% by weight and at least 20% of the sugar has been consumed.

7. A process according to claim 1, wherein the sugar amount in step (a) is 10–50% by weight of the cellulose amount and the sugar concentration during step (b) is 0.1–0.25% by weight.

8. A process according to claim 3, wherein the soluble sugar is lactose.

9. A process according to claim 1, wherein the concentration of sugar in step (b) is maintained at a value of 0.1 to 0.3% by weight.

10. A process according to claim 1, wherein a hyperproducing *Trichoderma reesei* strain is used.

* * * * *